United States Patent [19]

Wilkes

[11] 4,367,816
[45] Jan. 11, 1983

[54] TEAR STRIP FOR GAS STERILIZABLE PACKAGE AND PACKAGE

[76] Inventor: Kenneth R. Wilkes, 1410 E. 15th St., Los Angeles, Calif. 90021

[21] Appl. No.: 272,186

[22] Filed: Jun. 10, 1981

[51] Int. Cl.³ ...................... B65B 61/18; B65D 65/40; B65D 75/30
[52] U.S. Cl. .................................. 206/439; 206/484; 206/484.1
[58] Field of Search ............... 206/439, 438, 440, 484, 206/484.1, 484.2, 610, 607, 608, 828; 220/460, 461; 229/62

[56] References Cited

U.S. PATENT DOCUMENTS

| | | | | |
|---|---|---|---|---|
| 2,643,049 | 6/1953 | Bartelt | | 206/608 |
| 3,472,369 | 10/1969 | Schuster | | 206/438 |
| 3,761,013 | 9/1973 | Schuster | | 206/439 |
| 3,926,311 | 12/1975 | Laske | | 206/439 |
| 3,967,729 | 7/1976 | Tanner | | 206/440 |
| 4,057,144 | 11/1977 | Schuster | | 206/439 |
| 4,270,658 | 6/1981 | Schuster | | 206/439 |

*Primary Examiner*—William Price
*Assistant Examiner*—Jimmy G. Foster
*Attorney, Agent, or Firm*—Saul Epstein

[57] ABSTRACT

A fiber free, fast breathing tear strip for a gas sterilizable package which comprises a sandwich of a gas permeable membrane impervious to bacteria, and a perforated, or slit plastic sheet. The sandwich is peelably sealed around the access opening of a bag. One seam of the tear strip can be made non-peelable so that the tear strip becomes non-detachable. Particular embodiments of gas sterilizable packages which utilize the invented tear strip are disclosed.

24 Claims, 7 Drawing Figures

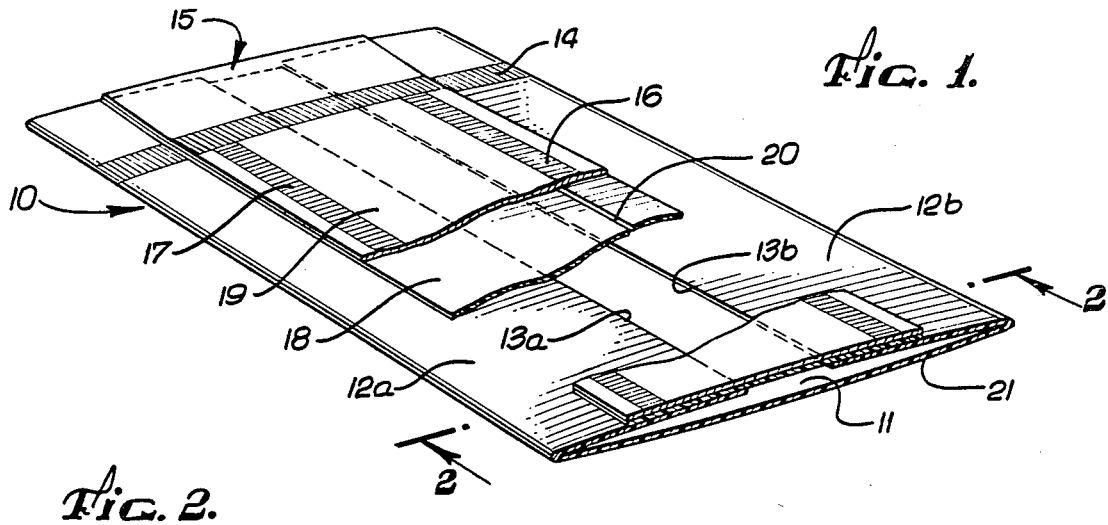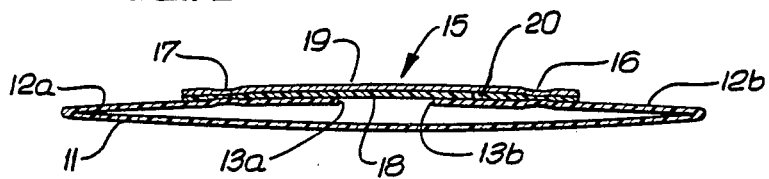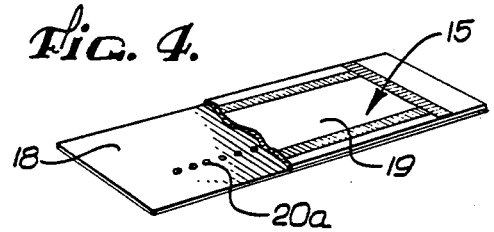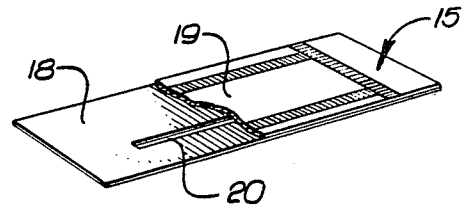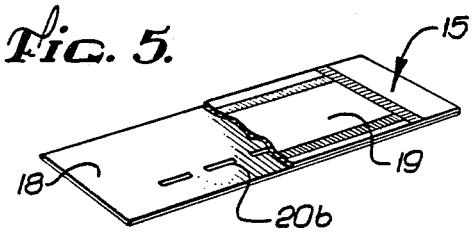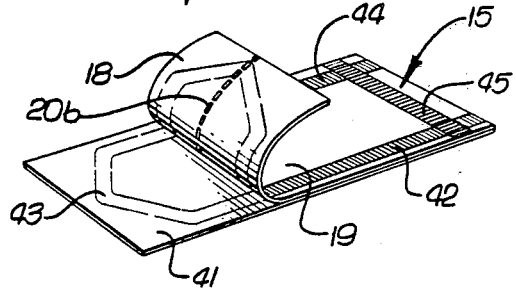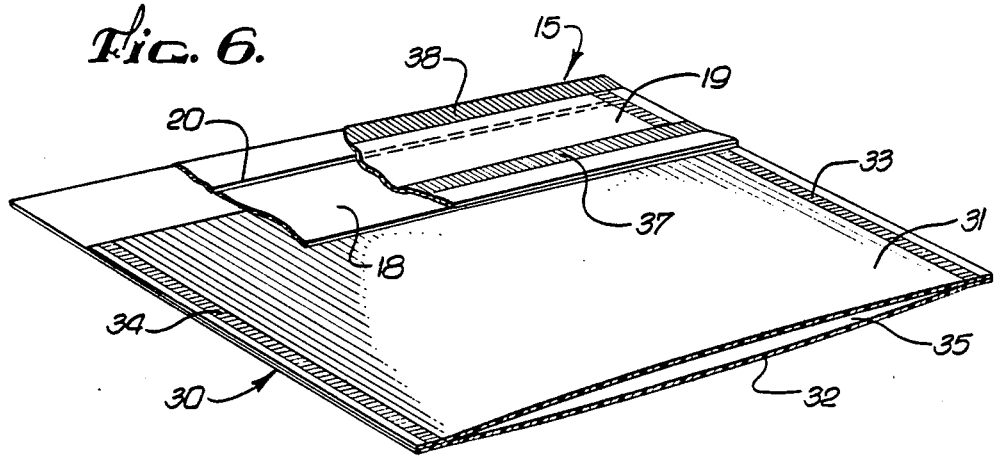

TEAR STRIP FOR GAS STERILIZABLE PACKAGE AND PACKAGE

BACKGROUND OF THE INVENTION

1. Field of the Invention

The present invention relates to gas sterilizable packages and more particularly to fiber free tear strips which are used to cover the access opening of the bag portion of such packages.

2. Prior Art

Gas sterilizable packages for maintaining the sterility of objects which are to be used, for example, in surgery, has been available for many years. Typically such packages utilize a bag fabricated from a flexible non-porous plastic such as polyethylene sealed to prevent the entry of bacteria. One portion of the bag is left open and is covered by a gas permeable membrane, i.e., a material which has pores small enough to prevent the passage of bacteria, but large enough to allow a sterilizing gas such as ethylene trioxide (ETO) to pass. There are a number of surgical grade papers and some plastic materials, for example, a DuPont product called Tyvek, which are suitable for this purpose. Sterilization is accomplished after sealing by exposure of the sealed package to the sterilizing gas. A typical prior art gas sterilizable package is described in U.S. Pat. No. 3,754,700 issued to Bonk.

The most convenient and practical embodiments of gas sterilizable packages being manufactured today use the gas permeable membrane as a cover for the access opening of the bag. That is, the gas permeable membrane is peelably adhered to the bag around the opening through which the contents are to be removed. When the bag contents are to be removed, the membrane, called a tear strip, is peeled off the bag and the contents spilled out or removed with tongs.

Sterilizable packages are typically fabricated from a continuous strip or strips of bag material on an intermittent feed heat sealing machine. The tear strip is sealed over the access opening at the same time as the other required seals are made. The bag is then cut from the supply strip leaving one seal unmade. At a later time the objects to be stored are inserted in the bag and the final seal made.

The sterilization process involves alternate cycles of pressure and vacuum using a sterilizing gas such as ETO which kills any bacteria inside the package. Since the bag itself is pinhole free and the tear strip is impervious to bacteria, the package can be stored in a non-sterile environment, yet the contents remain sterile.

The problem which has faced gas sterilizable package designers heretofore is that the papers commonly used for tear strips are easily abraded, and the access opening becomes contaminated with paper fibers, and with many bag designs, fibers even find their way into the bag. This problem has been alleviated in the past by either coating the tear strip with a peelable adhesive or calendering the paper so that it has a hard tight surface. Unfortunately, both of these methods impair the breathability of the paper. A typical coating will slow the breathing rate by a factor of three. A relatively heavy coating may be necessary since usually the faster the breathing rate the weaker the seal strength of the package.

The common measure of breathing rate is the number of seconds required for 100 cc of air to pass through one square inch of material. Uncoated papers have a breathing rate of less than 50 seconds, but when coated, the breathing rate may range from 100 to 300 seconds.

Until this invention, the packaging engineer had to choose the coating that would give the proper seal strength for the weight and bulk of the product and then would have to choose a sterilization cycle that would insure the proper penetration of the gas.

The packaging engineer was constantly faced with a compromise, if he had high seal strength that would insure that the product would be still sterile by the end use, he might not have a properly sterilized product because the gas has a hard time penetrating the coating. The cycle times for the sterilization process can range from as little as 8 hours for very fast breathing packages to over 24 hours for slow breathing packages. If the engineer chose a high seal strength, thus a slow breathing package, the sterilization cost can run three times as much. A third problem arises with a slow breathing package and that is residual sterilization gas staying inside the package. Small amounts of the gas will attach to the product unless the gas is vigorously purged through rapid pressure changes. These rapid pressure changes cause even more stress on the seals. An ideal tear strip for a gas sterilized medical product package would have a breathing rate of under 50 seconds with a seal strength of over 1 lb per inch of seal, and provide a clean fiber free sterile access opening for the product to be withdrawn from.

It is therefore an object of the present invention to provide a rapid breathing tear strip for a gas sterilizable package which has a high speed strength.

It is a further object of the present invention to provide a fiber free tear strip for a gas sterilizable package.

Other objects and advantages of the present invention will become apparent from the following specification and the drawings.

SUMMARY OF THE INVENTION

The invented tear strip disclosed in this application is a sandwich comprised of two layers of material, each selected to have certain desired properties. The two layers are heat sealed together, usually at the same time that the sandwich is heat sealed to the bag.

The outer, or top layer of the sandwich, is a surgical grade paper or other gas permeable membrane having relatively low resistance to gas flow but yet opaque to bacteria so as to maintain sterility. The inner, or bottom layer is a plastic sheet of a type which will form a peelable bond to the bag material being used, and an adequately strong bond to the top layer. The inner layer is perforated in a selected area within the seal lines which allows the sterilizing gas to pass freely.

There are many suitable materials which can be used in connection with the present invention, but for purposes of illustration, a combination of materials which have been found to work well with, for example, a bag fabricated from low density polyethylene sheet, includes a bottom sheet of high density polyethylene sheet coated on each side with a thin layer of a blend of ethyl vinyl acetate (EVA) and low density polyethylene, and a top sheet of surgical paper. The blend of EVA and low density polyethylene is adjusted so that its bond to the high density polyethylene sheet provides the desired peel strength.

The bond strength along one of the seal lines can be increased substantially by using a higher temperature heat sealing iron, or by heating the seam repeatedly.

When this is done, the tear strip becomes non-detachable, thereby reducing the loose item count in the surgical theater.

BRIEF DESCRIPTION OF THE DRAWINGS

FIG. 1 is a perspective view of one type of gas sterilizable package using the invented tear strip. The tear strip is shown with a broken away section to illustrate its construction.

FIG. 2 is a cross-sectional view of the package of FIG. 1 taken at 2—2 of FIG. 1.

FIG. 3 is a perspective view of one embodiment of the invented tear strip with the top layer partially broken away.

FIG. 4 is a perspective view of a second embodiment of the invented tear strip with a top layer partially broken away.

FIG. 5 is a perspective view of a third embodiment of the invented tear strip with the top layer partially broken away.

FIG. 6 is a perspective view of a second type of package utilizing the invented tear strip. The tear strip is shown partially broken away to illustrate its construction.

FIG. 7 is a perspective view of a third type of package utilizing the invented tear strip. In this figure the package is shown partially opened.

DETAILED DESCRIPTION OF THE INVENTION

Referring first to FIGS. 1 and 2 where a first embodiment of a tear strip according to the present invention is shown applied to a typical bag as used in the medical field. It should be understood, of course, that the invented tear strip can be used in connection with a wide variety of styles, shapes, and sizes of bags and the one shown in FIGS. 1 and 2 is only illustrative of the application of the present invention. The bag 10 is shown fabricated from a single sheet of plastic folded so as to form a bottom face 11 and two top faces 12a and 12b, the edges 13a and 13b of which form a slot in the top of the bag. The opening between edges 13a and 13b is the access opening of the bag through which the stored items are removed when the bag is opened. The edges 13a and 13b may butt or overlap if desired but more commonly a space is left so as to make removal of the bag contents easier. In production, bags such as those illustrated in FIGS. 1 and 2 are fabricated from a continuous strip of material with the individual bags cut off as the material is folded and seamed. One end of the bag is closed at the time of fabrication with heat seal 14. The other end is left open and is sealed with a similar heat seal after the items to be stored are inserted.

A tear strip 15 is heat sealed to the bag covering the slot between edges 13a and 13b. On one end, the tear strip is sealed to the bag 10 by heat seal 14, and on the other end by the heat seal made after filling the bag. Two additional heat seals 16 and 17 seal the tear strip 15 to faces 12a and 12b but do not seal the faces 12a and 12b to bottom 11.

According to the prior art the bag itself is made of a plastic material such as low density polyethylene and the tear strip is a single sheet of paper which is gas permeable but opaque to bacteria. As noted in the summary section of this application, fibers can abrade off paper unless it is treated to prevent such abrasion. Such treatment is undesirable since it reduces the breathability of the strip.

According to the present invention, the tear strip, a first embodiment of which is illustrated in FIG. 3, is a sandwich, one component of which is a sheet of plastic 18 having a slit 20 extending for a portion of its length. The slit is preferably off center for a reason which will be discussed later, but if desired the slit can be centered. While a single long slit is shown in the embodiment of the tear strip illustrated, it should be understood that other kinds of openings could be used within the spirit of the invention. For example, a plurality of small holes or short intermittent slits could be used to serve the function of the slit illustrated, i.e., to make the plastic sheet gas permeable but at the same time reduce the exposed area of a gas permeable membrane 19 which forms the second part of the tear strip sandwich. The alternate embodiments are illustrated in FIGS. 4 and 5 respectively.

The two parts of the tear strip are most conveniently made substantially the same size and shape and are sealed adjacent their periphery by heat seals 14, 16, 17, and a fourth seal adjacent to end 21 which is now shown. The seals 14, 16 and 17 may conveniently be made at the time of fabrication of the bag, these seals also serving to seal the tear strip to the bag as illustrated in FIGS. 1 and 2. Similarly, the seal adjacent to the end 21 may conveniently be made when the bag is sealed after filling. Some portion of the tear strip should extend outboard of one of the seals so as to provide a fingerhold area for peeling the tear strip off the bag. The fingerhold area illustrated is shown adjacent to seal 14.

As referred to previously, and as can be seen in FIG. 1, the slit 20 is off center of the sheet 18, and in fact, is enough off center so that it is adjacent to top face 12b rather than being in the slot area between edges 13a and 13b. This is preferable, but not essential, in that it affords extra isolation between membrane 19 and the inside of bag 10.

Many different materials are suitable for use in connection with the tear strip disclosed herein. In one typical specific example of the invention, the bag is made of low density polyethylene. Plastic sheet 18 is a co-extrusion of high density polyethylene with a thin layer of a blend of ethyl vinyl acetate (EVA) and low density polyethylene on each side of the high density polyethylene sheet. Membrane 19 is a surgical paper selected to have the desired breathing rate and strength. The proportions of EVA and low density polyethylene used to coat sheet 18 may be adjusted to obtain the desired bond strength between the EVA blend and the high density polyethylene base. A bond strength of 1 lb per inch of seal is a common value used and easily attainable. With such a bond strength, the tear strip is easily peeled from the bag, the EVA blend separating cleanly from the high density polyethylene base sheet and transferring to the low density polyethylene bag. The bond between the EVA blend and the paper membrane 19 is usually greater than the tear strength of the paper. An alternate material to paper for membrane 19 is a product marketed by DuPont called Tyvek. Tyvek is a plastic product which is gas permeable and commonly used by itself as a tear strip in prior art sterilizable bags. Uncoated Tyvek has a good breathing rate, but in order to attain a peelable seal it is necessary to coat the Tyvek. The breathing rate of a coated Tyvek is slower than the uncoated product by a factor in the range of about three to six. By using uncoated Tyvek in combination with a sheet 18 as described herein, the advantages of Tyvek, i.e., high puncture strength and water resistance, can be maintained together with the desired fast breathing rate.

A second style of bag to which the tear strip disclosed herein is adaptable is illustrated in FIG. 6. The bag 30 is comprised of two sheets 31 and 32 fastened together at their edges by heat seals 33 and 34. End 35 is left open until the bag is filled, after which it is sealed in the same manner as seals 33 and 34. Sheet 32 extends beyond the end of sheet 31 at end 36 to provide a seal area for tear strip 15. Seals 33, 34, 37 and 38 hold the tear strip over the opening at end 36 and prevent the entry of foreign matter or bacteria. Seal 37 is made only to sheet 31 and does not adhere sheet 31 to sheet 32. The seals 33, 34, 37 and 38 are made peelable as previously described so that the bag may be opened by merely grasping a free edge of tear strip 15 adjacent to seal 37 and peeling off.

It is generally desirable to keep the number of loose items in a surgical suite to a minimum so as to simplify the accounting normally used to assure that no foreign object finds its way into the patient. A non-detaching tear strip is therefore desirable. By making the bond strength of seal 38 substantially higher than the seals between the tear strip and the bag at 33, 34, and 37, such a non-detachable seal can be attained. The bond strength of seal 38 can be made high by several means, for example, by using a higher temperature sealing iron or by repeating the seal operation two or more times at seal 38. Similarly, any one of the seals sealing the tear strip 15 to the package illustrated in FIGS. 1 and 2 can be made non-detachable.

A third style sterilizable package to which the invented tear strip is applicable is illustrated in FIG. 7. The package as shown is a very common type, known as a chevron package, so called because of the chevron shaped seal at one end. According to the prior art, such a package is comprised of a bottom sheet of flexible plastic peelably sealed around its periphery to a tear sheet comprised of gas permeable paper or plastic (e.g., Tyvek). The space between the plastic and the paper is the storage volume for sterile articles. Access to the stored articles is had by simply peeling the tear sheet from the plastic sheet.

According to the present invention a chevron package can be fabricated with a flat plastic bottom sheet 41 which is heat sealed to a tear strip 15 fabricated as previously described and illustrated in FIG. 3, 4 or 5. Seals 42, 43, 44 and 45 enclose the storage area. For purposes of illustration, the package of FIG. 7 is shown after it has been opend and the contents removed rather than before any articles are placed inside as was done in FIGS. 1 and 6. Seal 45, which normally is made after the package is filled is therefore shown. Since the bag has been opened, seal 43 and parts of seals 42 and 44 have been broken. Seal 43 is shown chevron shaped which is very common in the prior art, but it can have other shapes such as semicircular or even be a straight seal. The tear strip 15 shown in FIG. 7 is shown fabricated with intermittent slits 20b as illustrated in FIG. 5. The intermittent slits 20b are shown continuing outside the sealed area to illustrate the fact that the integrity of the package will not be compromised thereby, seal 43 being made to provide the required barrier.

The tear seal can be made non-detachable by making seal 45 or the portions of seals 42 and 44 in the region of seal 45 non-peelable.

What has been described is a novel tear strip for a gas sterilizable package. Several embodiments have been described, but others within the spirit of the invention will readily occur to those skilled in the art and such are intended to be included within the scope of the invention as defined by the following claims.

I claim:
1. A tear strip for a gas sterilizable package of the type comprising a plastic bag having an access opening and a gas permeable tear strip peelably sealed to said bag around said access opening which comprises:
   a. a plastic sheet having a perforated area; and
   b. a gas permeable sheet sealed to said plastic sheet with a plurality of line seals enclosing said perforated area.
2. A tear strip as recited in claim 1 where the perforations in said perforated area comprises at least one slit.
3. A tear strip as recited in claim 1 where the perforations in said perforated area comprises a plurality of small holes.
4. A tear strip as recited in claims 1, 2 or 3 where said plastic sheet is high density polyethylene with a coating on at least the side of said plastic sheet facing said bag comprised of a blend of low density polyethylene and ethyl vinyl acetate.
5. A gas sterilizable package which comprises:
   (a) two substantially rectangular plastic sheets in face to face relationship, one edge of the first of said sheets overhanging the complementary edge of the second of said sheets, the space between the overhanging portion of said first sheet and said complementary edge of said second sheet defining an access opening;
   (b) a plurality of line seals sealing the first of said plastic sheets to the second of said plastic sheets along the three edges of said sheets not including said access opening; and
   (c) a tear strip peelably sealed to the overhanging portion of said first sheet and the complementary edge of said second sheet, said tear sheet comprising:
      i. a third plastic sheet having a perforated area, and
      ii. a gas permeable sheet sealed to said plastic sheet with a plurality of line seals enclosing said perforated area.
6. A gas sterilizable package as recited in claim 5 where the perforations in said perforated area comprises at least one slit.
7. A gas sterilizable package as recited in claim 5 where the perforations in said perforated area comprises a plurality of small holes.
8. A gas sterilizable package as rectied in claims 5, 6, or 7 where said third plastic sheet is high density polyethylene with a coating on at least the side of said third plastic sheet facing said first and second plastic sheets comprised of a blend of low density polyethylene and ethyl vinyl acetate.
9. A gas sterilizable package as recited in claims 5, 6, or 7 wherein a portion of the area sealing said tear strip to said overhanging portion of said first sheet is non-peelable.
10. A gas sterilizable package which comprises:
   (a) a first single substantially rectangular plastic sheet folded along two parallel lines whereby a bottom portion and two top portions are formed, the space between two opposite edges of said sheet parallel to said fold lines defining an access opening;
   (b) sealing means sealing said top portions to said bottom portion adjacent the edges of said sheet perpendicular to said fold lines; and

(c) a tear strip covering and peelably sealed to said first plastic sheet around said access opening, said tear strip comprising:
   i. a second plastic sheet having a perforated area; and
   ii. a gas permeable sheet sealed to said plastic sheet with a plurality of line seals enclosing said perforated area.

11. A gas sterilizable package as recited in claim 10 where the perforations in said perforated area comprises at least one slit.

12. A gas sterilizable package as recited in claim 11 where the perforations in said perforated area comprises a plurality of small holes.

13. A gas sterilizable package as recited in claims 10, 11, or 12 where said third plastic sheet is high density polyethylene with a coating on at least the side of said second plastic sheet facing said first plastic sheet is comprised of a blend of low density polyethylene and ethyl vinyl acetate.

14. A gas sterilizable package as recited in claims 10, 11, or 12 wherein a portion of the area sealing said tear strip to said first sheet is non-peelable.

15. A gas sterilizable package which comprises:
(a) a first wall of plastic sheet material;
(b) a second wall comprising;
   i. a plastic sheet having a perforated area, and
   ii. a gas permeable sheet sealed to said plastic sheet with a plurality of line seals enclosing said perforated area; and
(c) means for peelably sealing said first wall to said second wall with a plurality of line seals.

16. A gas sterilizable package as recited in claim 15 where the perforations in said perforated area comprises at least one slit.

17. A gas sterilizable package as recited in claim 15 where the perforations in said perforated area comprises a plurality of small holes.

18. A gas sterilizable package as recited in claims 15, 16 or 17 where said perforated plastic sheet is high density polyethylene with a coating on at least the side of said perforated plastic sheet facing said first wall comprised of a blend of low density polyethylene and ethyl vinyl acetate.

19. A gas sterilizable package as recited in claims 15, 16, or 17 wherein a portion of the area sealing said first wall to said second wall is non-peelable.

20. A gas sterilizable package which comprises:
(a) a plastic bag having an access opening;
(b) a gas permeable tear strip peelably sealed to said bag around said access opening, said tear strip comprising:
   i. a plastic sheet having a perforated area, and
   ii. a gas permeable sheet sealed to said plastic sheet with a plurality of line seals enclosing said perforated area.

21. A gas sterilizable package as recited in claim 20 where the perforations in said perforated area comprises at least one slit.

22. A gas sterilizable package as recited in claim 20 where the perforations in said perforated area comprises a plurality of small holes.

23. A gas sterilizable package as recited in claims 20, 21, or 22 where said plastic sheet is high density polyethylene with a coating on at least the side of said plastic sheet facing said bag comprised of a blend of low density polyethylene and ethyl vinyl acetate.

24. A gas sterilizable package as recited in claims 20, 21, or 22 wherein a portion of the area sealing said tear strip to said second wall is non-peelable.

* * * * *